United States Patent
Zang et al.

(10) Patent No.: US 8,629,108 B2
(45) Date of Patent: Jan. 14, 2014

(54) RHEUMATOID ARTHRITIS T CELL VACCINE

(75) Inventors: Jingwu Zhang Zang, Shanghai (CN); Guangjie Chen, Shanghai (CN); Hong Nie, Shanghai (CN); Ningli Li, Shanghai (CN)

(73) Assignee: Opexa Therapeutics, Inc., The Woodlands, TX (US)

( * ) Notice: Subject to any disclaimer, the term of this patent is extended or adjusted under 35 U.S.C. 154(b) by 828 days.

(21) Appl. No.: 12/306,894

(22) PCT Filed: Jun. 27, 2007

(86) PCT No.: PCT/US2007/072277
§ 371 (c)(1),
(2), (4) Date: Jan. 11, 2010

(87) PCT Pub. No.: WO2008/002996
PCT Pub. Date: Jan. 3, 2008

(65) Prior Publication Data
US 2010/0111982 A1  May 6, 2010

Related U.S. Application Data

(60) Provisional application No. 60/805,951, filed on Jun. 27, 2006.

(51) Int. Cl.
*A61K 38/20* (2006.01)
(52) U.S. Cl.
USPC ........................................ 514/16.6
(58) Field of Classification Search
None
See application file for complete search history.

(56) References Cited

FOREIGN PATENT DOCUMENTS

WO  WO 2005084137 A2 *  9/2005

OTHER PUBLICATIONS

Mimran et al., Int Rev Immunol. May-Aug. 2005;24(3-4):159-79.*
Gattinoni et al., J Clin Invest. Jun. 2005;115(6):1616-26.*
Ehrenstein et al., J Exp Med. Aug. 2, 2004;200(3):277-85.*
Hong et al., Proc Natl Acad Sci U S A. Mar. 28, 2006;103(13):5024-9 and pp. 1-3 of supplemental supporting information.*
Breedveld et al. (Immunological Reviews 1995, No. 144, pp. 5-16).*
International Search Report from parent international application No. PCT/US07/72277, issued by ISA/US on Aug. 25, 2008.
Written Opinion of the International Searching Authority from parent international application No. PCT/US07/72277, issued by ISA/US on Aug. 25, 2008.
Chen, G, et al. Vaccination with selected synovial T cells in rheumatoid arthritis. Arthritis and Rheumatism, 2007;56 (2):453-63.
Hermans, G, et al. Cellular and humoral immune responses against autoreactive T cells in multiple sclerosis patients after T cell vaccination. Journal of Autoimmunity, 1999;13:233-46.
Van Laar, JM, et al. "Towards T cell vaccination in rheumatoid arthritis," Mechanisms of Immune Regulation (Granstein RD, ed.), 1994;58:206-35.

* cited by examiner

*Primary Examiner* — Zachary Skelding
(74) *Attorney, Agent, or Firm* — Todd Lorenz; Arnold & Porter LLP (57) ABSTRACT

Described herein is an activated synovial autoreactive T cell and compositions thereof. Methods or preparing T cell compositions that may be used for treating rheumatoid arthritis are also described.

2 Claims, 8 Drawing Sheets

FIG. 1

| Gene | Sequence 5'→3' | Amplicon (bp) | SEQ ID NOS: |
|---|---|---|---|
| IFN-γ | TCAGCTCTGCATCGTTTTGG (forward)<br>GTTCCATTATCCGCTACATCTGAA (reverse) | 120 | 1<br>2 |
| TNF-α | TCTTCTCGAACCCCGAGTGA<br>CCTCTGATGGCACCACCAG | 151 | 3<br>4 |
| IL-10 | GTGATGCCCCAAGCTGAGA<br>CACGGCCTTGCTCTTGTTTT | 138 | 5<br>6 |
| IL-5 | ATGCCATCCCCACAGAAATTC<br>CCTCAGAGTCTCATTGGCTATCAG | 100 | 7<br>8 |
| TGF-β | CAGCAACAATTCCTGGCGATA<br>AAGGCGAAAGCCCTCAATTT | 136 | 9<br>10 |
| IL-12 | TGGAGTGCCAGGAGGACAGT<br>TCTTGGGTGGGTCAGGTTTG | 147 | 11<br>12 |
| GAPDH | GAAGGTGAAGGTTCGGAGTC<br>GAAGATGGTGATGGGATTTC | 187 | 13<br>14 |

FIG. 2

| T cell vaccine patient no. | %CD4+ T cells | %CD8+ T cells | Dominant TCR BV genes* | Cytokine profile | | |
|---|---|---|---|---|---|---|
| | | | | IFN-γ (pg/ml) | TNF-α (pg/ml) | IL-10 (pg/ml) |
| RA-1 | 18.08 | 76.48 | BV14 | 1910.76 | 380.57 | 5.23 |
| RA-2 | 16.76 | 81.63 | BV14 | 204.18 | 131.28 | 3.99 |
| RA-3 | 14.06 | 82.09 | BV13, BV17 | 190.44 | 150.85 | 5.30 |
| RA-4 | 28.16 | 61.95 | BV14 | 57.24 | 16.98 | 3.76 |
| RA-5 | 21.26 | 68.63 | BV14 | 523.03 | 505.00 | 8.60 |
| RA-6 | 35.47 | 62.65 | BV13, BV6 | 263.49 | 49.48 | 68.70 |
| RA-7 | 32.96 | 35.65 | BV13, BV17 | 105.91 | 70.00 | 5.50 |
| RA-8 | 32.03 | 61.73 | BV14, BV17 | 50.60 | 46.13 | 7.53 |
| RA-9 | 48.78 | 57.85 | BV2, BV17 | 242.76 | 50.38 | 7.38 |
| RA-10 | 4.26 | 86.88 | BV17 | 1368.93 | 428.00 | 5.44 |
| RA-11 | 20.20 | 75.47 | BV6 | 180.11 | 86.90 | 5.30 |
| RA-12 | 35.47 | 62.65 | BV13 | 260.48 | 167.88 | 5.30 |
| RA-13 | 31.75 | 55.26 | BV14,BV6 | 320.12 | 200.09 | 7.03 |
| RA-14 | 32.58 | 49.75 | BV2 | 550.00 | 316.04 | 5.19 |
| RA-15 | 16.29 | 80.79 | BV6,BV13 | 439.89 | 223.46 | 5.50 |
| Mean | 25.87 ±2.91 | 66.63 ±3.64 | | 444.53 ±133.75 | 188.20 ±39.62 | 9.98 ±4.21 |

|  | Month 3 | Month 6 | Month 9 | Month 12 |
| --- | --- | --- | --- | --- |
| *ACR response rate (%)* | | | | |
| ACR 20 | 73.3 | 93.3 | 100 | 73.3 |
| ACR 50 | 33.3 | 73.3 | 80.0 | 66.7 |
| ACR 70 | 13.3 | 40.0 | 60.0 | 53.3 |
| *Mean improvement (% decrease) from baseline in the ACR components[b]* | | | | |
| Tender joints | 70.7** | 73.3** | 77.3** | 74.0** |
| Swollen joints | 67.1** | 83.6** | 86.8** | 85.5** |
| Pain score | 45.2** | 69.4** | 76.3** | 61.1** |
| Physical function | 71.1** | 80.0** | 73.3** | 67.8** |
| Patient's assessment | 46.2** | 68.1** | 76.3** | 66.2** |
| Physician's assessment | 46.2** | 68.1** | 76.3** | 66.2** |
| C-reactive protein (CRP) | 50.5 | 68.1* | 68.9* | 63.8* |
| Erythrocyte sentiment rate (ESR) | 26.5* | 48.3* | 37.2* | 31.9* |
| Rheumatoid factor (RF) | 40.5 | 64.5* | 56.6* | 70.4* |

[A] A clinical response was defined according to the American College of Rheumatology (ACR) definition of a 20 percent improvement (ACR 20), indicating a decrease of at least 20 percent in the number of both tender joints and swollen joints, along with a 20 percent improvement in at least three of the following: the patient's assessment of disease status, the patient's assessment of pain, the patient's estimate of function, the physician's assessment of disease status, and the serum of C-reactive protein or ESR. The percentage of patients with an improvement of 50 percent (ACR 50) and 70 percent (ACR 70), according to the ACR criteria, were assessed in a similar manner.

[B] Values were carried forward from the efficacy observation at Month 3, Month 6, Month 9 and Month 12

\* $P < 0.05$ for the comparison with baseline observation

\*\* $P < 0.01$ for the comparison with baseline observation

RHEUMATOID ARTHRITIS T CELL VACCINE

CROSS-REFERENCES TO RELATED APPLICATIONS

This application is the U.S. National Stage of International Application No. PCT/US2007/072277, filed Jun. 27, 2007, which claims the benefit of U.S. Provisional Patent Application No. 60/805,951, filed Jun. 27, 2006.

BRIEF DESCRIPTION OF THE SEQUENCE LISTING

Reference is made to the appendix submitted on the electronic .txt file submitted herewith. The file named "Sequence.txt" (4 KB, Apr. 10, 2009), is a Sequence Listing in accordance with 37 C.F.R. §§1.821-1.825, the contents of which are incorporated by reference herein.

BACKGROUND

1. Field of the Invention

The present invention relates to T cell vaccines and methods of preparing these vaccines. The T cell vaccines may be used to treat autoimmune diseases, such as rheumatoid arthritis (RA).

2. Description of Related Art

Rheumatoid arthritis (RA) is a chronic disorder of unknown origin with variable courses of disease and is an autoimmune disease associated with abnormal immunity. The majority of patients with RA have a progressive course which leads to destruction of joint tissue, instability of joints, loss of function and mobility, and increased mortality. Patients suffering from rheumatoid arthritis have joints that are severely infiltrated with leukocytes such as lymphocytes, and in which pannus forms due to hyperproliferation of synovial cells. Although various mechanisms of rheumatoid arthritis have been proposed to explain the cause of the disease, including heredity, microbial infection, or involvement of various cytokines and chemokines, the precise onset mechanism is not known.

At present, RA can be somewhat controlled but not cured. The goal of treatment is relief of symptoms and keeping the disease from getting worse. The goals of most treatments for rheumatoid arthritis are to relieve pain, reduce inflammation, slow or stop the progression of joint damage, and improve a person's ability to function. Current approaches to treatment include lifestyle changes, medication, surgery, and routine monitoring and care. Standard RA therapy includes the use of immunomodulators, biologic agents, and corticosteroids, all of which have limited efficacy and carry significant risk of toxicity.

T cell vaccination is a promising therapy for T cell-mediated autoimmune diseases, such as multiple sclerosis (MS). The T cell vaccination strategy is based on administering a patient attenuated autoreactive T-cells, which may stimulate the patient's immune system to target the pathological autoreactive T-cells. A T cell vaccine is produced by activating and expanding mononuclear cells derived from the patient with autoreactive antigens. In MS, immunodominant myelin antigen epitopes from myelin proteins, such as MBP, PLP and MOG, may be used to produce the vaccine. T-cell vaccination is currently not available as a therapy for RA, because autoreactive antigens necessary to produce the vaccine have yet to be identified. Thus, there remains a need for treatments for arthritis.

SUMMARY

An isolated activated synovial autoreactive T cell is provided. A composition comprising the T cell is also provided. The composition may comprise greater than about 1 million of the T cell. The T cells of the composition may secrete TNF-α and γ-interferon, they may comprise at least 4% CD4+ T cells, they may comprise at least 4% CD8+ T cells, or they may be characterized by a combination thereof. The T cells of the composition may be attenuated. Attenuation may be by gamma irradiation.

A method of preparing a T cell composition is also provided. A sample derived from synovial fluid isolated from a subject may be provided. The sample may comprise activated T cells. The activated T cells may be expanded. The T cells may be activated by contacting the T cells with IL-2.

The T cell composition may be prepared in the presence of attenuated mononuclear cells isolated from a subject. The mononuclear cells may be peripheral blood mononuclear cells. The mononuclear cells may be attenuated by irradiation. The attenuated mononuclear cells may be derived from the same subject as the synovial fluid mononuclear cells.

A method of treating a patient with rheumatoid arthritis is also provided. A patient in need of treatment may be administered the T cell composition.

BRIEF DESCRIPTION OF THE DRAWINGS

FIG. 6 shows changes in TCR BV gene repertoire and characterization of BV2+ T cells. A. At months 0, 3, 6, 9 and 12, TCR BV gene expression was analyzed quantitatively by real-time PCR using specific primers for 25 BV genes (X-axis). The TCR BV gene distribution patterns are presented as mean % expression of each BV gene relative to BC expression on the Y-axis. Asterisks represent significant differences in TCRBV gene expression between baseline and at the indicated time point after T cell vaccination and between the individual BV gene expression and that of other BV genes (*p<0.05, **p<0.01). B. PBMC specimens were obtained from baseline (Before) and at 9 months or 12 months after T cell vaccination and analyzed for Vb2 expression by flow cytometry using specific monoclonal antibodies or an isotype-matched control antibody. The profiles shown were representative of six individual sample analyses. Both Vb2+ and Vb2– T cell fractions obtained from 15 patients were examined for the expression of Foxp3 by real-time PCR analysis (C), the frequency of IL-10 secreting T cells by ELISPOT (D) and the inhibitory activity in functional assays (E).

FIG. 8 provides Table 3, which shows the clinical assessment of T cell vaccinated RA patients.

DETAILED DESCRIPTION

It is desirable to make a vaccine against autoreactive T cells that are pathogenic in RA. As described above, it has not been possible to produce a T cell vaccine for treating RA due to a lack of knowledge of the pathological autoreactive antigens with which to activate T cells. Herein is provided, among other things, a vaccine derived from an autoreactive T cell that is pathogenic in RA. The vaccine may be produced without requiring knowledge of the relevant autoreactive antigens. The need to identify autoreactive antigens may be bypassed by deriving the T cell from the synovium.

1. DEFINITIONS

The terminology used herein is for the purpose of describing particular embodiments only and is not intended to be limiting. As used in the specification and the appended claims, the singular forms "a," "an" and "the" include plural referents unless the context clearly dictates otherwise.

"Peptide" or "polypeptide" may mean a linked sequence of amino acids and may be natural, synthetic, or a modification or combination of natural and synthetic amino acids.

"Treatment" or "treating," when referring to protection of an animal from a disease, may mean preventing, suppressing, repressing, or completely eliminating the disease. Preventing the disease involves administering a composition of the present invention to an animal prior to onset of the disease. Suppressing the disease involves administering a composition of the present invention to an animal after induction of the disease but before its clinical appearance. Repressing the disease involves administering a composition of the present invention to an animal after clinical appearance of the disease.

2. T CELLS

A T cell is provided. The T cell may be derived from a subject, which may suffer from or be at risk for RA. The T cell may be derived from the synovium. The synovium may be tissue. The synovium may also be fluid. The T cell may be activated. The T cell may also be autoreactive. The T cell may recognize "self" (autoreactive) antigens, as well as foreign antigens. The autoreactive antigens may be pathogenic in RA. As described below, the activated T cell may be expanded to produce sufficient numbers of autoreactive T cells that may be used to formulate a vaccine.

a. T Cell Composition

The T cell may be provided in a composition, which may comprise a plurality of the T cells. The number of T cells may be at least 5 million, 10 million, 15 million, 20 million, 25 million, 30 million, 45 million, 50 million, 65 million, or 80 million.

(1) Activated T Cell Markers

The T cell may express CD3, CD4, CD8, CD25, CD69, CD71, CD127 or a combination thereof. The T cell may secrete cytokines. The secreted cytokines may be IL-2, IL-3, γ-interferon, TGF-β, TNF-α or a combination thereof.

(2) Activated T Cell Cyokines

The T cell may also secrete a cytokine. The activated cell may be a Th cell. The Th cell may secrete γ-interferon. The Th cell may also secrete TNF-α. The Th cell may also secrete IL-12.

(3) T Cell Receptor BV Genes

The composition of T cells may be enriched for expression of a BV gene compared to an original sample. A BV gene encodes part of the variable region of the TCR protein of a T cell. Use of different BV genes in the TCR of a T cell may lead to T cells with different binding specificities for an antigen. The expressed BV gene may be enriched in the rheumatoid synovium.

Depending on the genotype of the subject from whom the T cell is derived, different specific BV genes may have elevated expression levels relative to other BV genes. The BV gene may be BV2. The BV gene may be BV6. The BV gene may be BV13. The BV gene may be BV14. The BV gene may also be BV17. The enrichment for BV14 and BV17, individually or collectively, may be to a level greater than about 4%, 10%, 20%, 30%, 40%, or 50%.

(4) Cytotoxic T Cells

The composition of T cells may comprise CD8+ T cells. The percentage of CD8+ (cytotoxic) T cells among the plurality of activated T cells may be to a level collectively greater than approximately 4%, 10%, 20%, 30%, 40%, 50%, or 60%.

The composition of T cells may also comprise CD4+ T cells. The percentage of CD4+ T cells among the plurality of activated T cells may be to a level collectively greater than around 4%, 10%, 20%, 30%, 40%, 50%, or 60%.

3. PREPARING T CELLS a. Expanding Activated T cells

The T cell may be derived from a sample comprising synovial mononuclear cells isolated from a subject. The sample may be derived from synovial fluid specimens by Ficoll-Hypaque gradient separation. Alternatively, the sample may also be derived from synovial membranes that have been enzymatically digested. For example, the mononuclear cells from synovial membranes (tissues) may be prepared by collagenase, dispase, and DNase digestion of membranes. The sample may comprise activated T cells. The sample may be cultured.

The T cell may be stimulated to proliferate (i.e., expanded). The T cell may undergo recurrent expansion cycles. Expansion cycles may be carried out for 7-10 days. The T cell may be propagated in expansion cycles until the total cell number reaches a desirable level. The T cell may be cryopreserved.

The T cell may also be prepared in the presence of additional mononuclear cells, which may be autologous. The mononuclear cells may also be derived from a subject who is different from the subject from whom the synovial fluid mononuclear cells are derived, but who is compatible to donate mononuclear cells to the subject from whom the synovial fluid mononuclear cells are derived. The ratio of the number of T cells in the T cell composition to the number of mononuclear cells may be around 1 to 500. The mononuclear cells may be peripheral blood mononuclear cells (PBMCs). The mononuclear cells may be viable. The mononuclear cells may also be attenuated.

The T cell may be expanded in the presence of a protein. The protein may be IL-2, IL-7, IL-12, IL-15, IL-21, or a combination thereof. The T cell may also be expanded in contact with a mitogen or superantigen. The mitogen or superantigen may be phytohaemagglutinin (PHA), Concavalin A (ConA), Phorbol 12-myristate 13-acetate (PMA)/Ionomycin, CytoStim, anti-CD3/anti-CD28 (antibodies alone or in conjugation to a microbead), or a combination thereof. The protein may also be used in combination with the mitogen or superantigen.

b. Attenuation

The T cell may be attenuated. The T cell may be attenuated in the presence of human serum albumin. Attenuated may be by any method that makes the T cell replication incompetent yet viable. For example, the T cell may be attenuated by irradiation such as gamma irradiation or by chemical inactivation.

c. Vaccine

The T cell may be formulated as a vaccine. The vaccine may also comprise T cell membranes or fragments thereof.

d. Formulation

The vaccine may be in the form of liquid formulations including, but not limited to, aqueous or oily suspensions, solutions, emulsions, syrups, and elixirs. The vaccine may also be formulated as a dry product for constitution with water or other suitable vehicle before use. Such liquid preparations may contain additives including, but not limited to, suspending agents, emulsifying agents, nonaqueous vehicles and preservatives. Suspending agents include, but are not limited to, sorbitol syrup, methyl cellulose, glucose/sugar syrup, gelatin, hydroxyethylcellulose, carboxymethyl cellulose, aluminum stearate gel, and hydrogenated edible fats. Emulsifying agents include, but are not limited to, lecithin, sorbitan monooleate, and acacia. Nonaqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid.

The vaccine may also be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, acacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate). Tablets may be coated according to methods well known in the art.

The vaccine may also be formulated as suppositories, which may contain suppository bases including, but not limited to, cocoa butter or glycerides. The vaccine may also be formulated for inhalation, which may be in a form including, but not limited to, a solution, suspension, or emulsion that may be administered as a dry powder or in the form of an aerosol using a propellant, such as dichlorodifluoromethane or trichlorofluoromethane. The vaccine may also be formulated transdermal formulations comprising aqueous or nonaqueous vehicles including, but not limited to, creams, ointments, lotions, pastes, medicated plaster, patch, or membrane.

The vaccine may also be formulated for parenteral administration including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The formulation may also comprise an adjuvant. The composition may also be provided in a powder form for reconstitution with a suitable vehicle including, but not limited to, sterile, pyrogen-free water.

The vaccine may also be formulated as a depot preparation, which may be administered by implantation or by intramuscular injection. The vaccine may be formulated with suitable polymeric or hydrophobic materials (as an emulsion in an acceptable oil, for example), ion exchange resins, or as sparingly soluble derivatives (as a sparingly soluble salt, for example).

e. Rheumatoid Arthritis Treatment

The vaccine may be used to treat a patient with rheumatoid arthritis.

f. Mode of Administration

The vaccine may be administered in any manner including, but not limited to, orally, parenterally, sublingually, transdermally, rectally, transmucosally, topically, via inhalation, via buccal administration, intrapleurally, or combinations thereof. Parenteral administration includes, but is not limited to, intravenous, intraarterial, intraperitoneal, subcutaneous, intramuscular, intrathecal, and intraarticular. Transmucosally administration includes, but is not limited to intranasal. For veterinary use, the composition may be administered as a suitably acceptable formulation in accordance with normal veterinary practice. The veterinarian can readily determine the dosing regimen and route of administration that is most appropriate for a particular animal.

The vaccine may be administered prior to, after or simultaneously with a second vaccine capable of treating an immunological disorder. The vaccine may be administered from about 1 hour to about 48 hours prior to or after exposure to the vaccine.

g. Dosage

A therapeutically effective amount of the vaccine required for use in therapy varies with the nature of the condition being treated, the length of time that induction of a response to the vaccine is desired, and the age and the condition of the patient, and is ultimately determined by the attendant physician. In general, however, doses employed for adult human treatment typically are in the range of 0.01 µg/kg to about 50 mg/kg. The dose may be about 0.1 µ/kg to about 5 mg/kg. The desired dose may be conveniently administered in a single dose, or as multiple doses administered at appropriate intervals, for example as two, three, four or more subdoses per day for a single day or over a course of many days. Multiple doses may be desired, or required, because response to vaccination may be decreased once the vaccine is no longer administered.

The dosage of the agent may be at any dosage including, but not limited to, about 0.01 µg/kg, 0.05 µg/kg, 0.1 µg/kg, 0.5 µg/kg, 1 µg/kg, 5 µg/kg, 10 µg/kg, 50 µg/kg, 100 µg/kg, 500 µg/kg, 1 mg/kg, 5 mg/kg, 10 mg/kg, or 50 mg/kg.

The dosage of the vaccine may also be approximately $1\times10^6$, $2\times10^6$, $3\times10^6$, $4\times10^6$, $5\times10^6$, $10\times10^6$, $15\times10^6$, $20\times10^6$, $25\times10^6$, $30\times10^6$, $35\times10^6$, $40\times10^6$, $45\times10^6$, $50\times10^6$, $55\times10^6$, $60\times10^6$, $65\times10^6$, $70\times10^6$, $75\times10^6$, $80\times10^6$, $85\times10^6$, or $90\times10^6$ attenuated T cells.

h. IL-2 Receptor Peptide

The vaccine may be administered together with a IL-2 receptor peptide.

The present invention has multiple aspects, illustrated by the following non-limiting examples.

Example 1

Preparation and Characteristics of the T Cell Vaccine

1. Preparation of the T Cells

Synovial fluid samples were drawn from 15 subjects with rheumatoid arthritis (RA), as diagnosed using criteria of the American College of Rhumatology (ACR). Mononuclear cells were prepared from the specimens by Ficoll-Hypaque gradient separation. The resulting mononuclear cells were incubated in 96 well round-bottom microtiter plates at 100 cells per well with irradiated autologous peripheral blood mononuclear cells (PBMC, 50,000 cells/well) as a source of accessory cells, and in the presence of 50 IU/ml recombinant IL-2 (Proleukine®, Chiron). The culture medium used was RPMI 1640, containing 5% human AB serum (Shanghai Blood Center). After 7-10 days and culture medium changes with 50 IU/ml recombinant IL-2, cells in growth-positive wells were collected and expanded in the presence of 2 µg/ml of phytohemagglutanin (PHA) and 100 IU/ml recombinant IL-2 to reach a T cell vaccine stock of approximately 80 million cells, which were then divided into identical aliquots and cryopreserved for subsequent treatment of subjects. One of the aliquots was used for characterizing the T cells.

2. T Cell Phenotypic Characteristics

Phenotypic expression of the T cell vaccine was characterized by flow cytometry. Approximately 100,000 cells were washed in PBS containing 1% fetal bovine serum (FBS) and resuspended in 100 µL PBS-FBS with fluorochrome-labeled antibodies or isotype antibody controls. All antibodies, including CD4, CD8, CD25, and γ2a-FITC/γ1-PE were obtained from BD Biosciences. After incubation for 30 min on ice, the T cells were washed 3 times in PBS-FBS, and fixed in 1% paraformaldehyde. Percentage of positive stained cells was analyzed using a FACS Aria instrument (BD Biosciences).

The prepared T cells comprised an average of 25.9% and 66.6% CD4+ and CD8+ cells, respectively. In comparison, the T cells from the original synovial fluid specimens comprised an average of 35.4% and 43.2% CD4+ and CD8+ T cells, respectively.

3. T Cell Receptor (TCR) BV Gene Distribution

In another experiment, total RNA was isolated using RNeasy Mini Kit (Qiagen) from T cells. Genomic DNA was removed from total RNA prior to cDNA synthesis using a RNase-free DNase Set (Qiagen). First-strand cDNA synthesis was performed for each RNA sample using Sensiscript RT Kit (Qiagen). Random hexamers were used to prime cDNA synthesis. 25 TCR BV and TCR BC gene specific primer were synthesized as previously described (Sun et al., Brain 2004; 127:996-1008). cDNA was synthesized from RNA using random primers and Superscript II (Invitrogen) in a 10 ml reaction.

TCR BV gene expression was analyzed by real-time quantitative PCR. An internal reference control for BV-BC amplification and a non-template control containing no cDNA were added to each reaction. Real-time PCR was performed in 384-well optical PCR plates on an ABI 7000 Sequence Detection System (Applied Biosystems). Briefly, an aliquot of cDNA sample (0.5 ml) was mixed with 25 pairs of BV-specific primers and 1 pair of BC primers (0.1 mM in final solution), respectively, together with SYBR Green PCR Master Mix (Applied Biosystems) to a final reaction volume of 10 ml. The reaction was performed at 50° C. for 2 min and at 95° for 10 min as hot start activation, which was followed by 40 cycles of reaction at 95° C. for 15 sec and at 60° C. for 1 min. The expression of individual BV genes were calculated based on signal intensity of the PCR reactions according to the following formula: TCR BVn (%)=$[2^{-(BVn\ Ct-BC\ Ct)} \times 100/\Sigma(2^{-(BV1-25\ Ct-BC\ Ct)} \times 100)] \times 100$, where Ct refers to the threshold cycle.

The TCR BV gene distribution pattern of the T cell vaccine was clustered in BV14 (mean 41.3% in 6/15 samples) and BV17 (mean 18.4% in 5/15 samples), compared to other BV genes.

4. T Cell Cytokine and Foxp3 Characteristics

In another experiment serum cytokines were determined quantitatively using ELISA kits obtained from BD Pharmagen. Briefly, 96-well microtiter plates were pre-coated overnight at 4° C. with 2 µg per well of respective mouse capturing monoclonal antibody (mAb) in PBS. Wells were than blocked at 37° C. for 2 hours with 2% BSA-PBS and washed three times with cold washing solution. Each samples and its control were added to the adjacent wells and incubated for 2 hours with a biotinylated detecting antibody. Plates were washed and incubated for 30 min with streptavidin-conjugated horseradish peroxidase prior to color development. The detection limits for all cytokines were <15 pg/ml in all assays.

The T cells of the T cell vaccine preferentially produced TNFα (188.2±4 pg/mL) and γ-interferon (444.5±133 pg/mL), with IL-10 levels below the lower limit of detection (i.e., IL-10 levels were <15 pg/mL). In addition, the T cells did not exhibit detectable inhibitory or cytotoxic effects on autologous T cells induced by CD3/CD28 stimulation.

Figure 2:
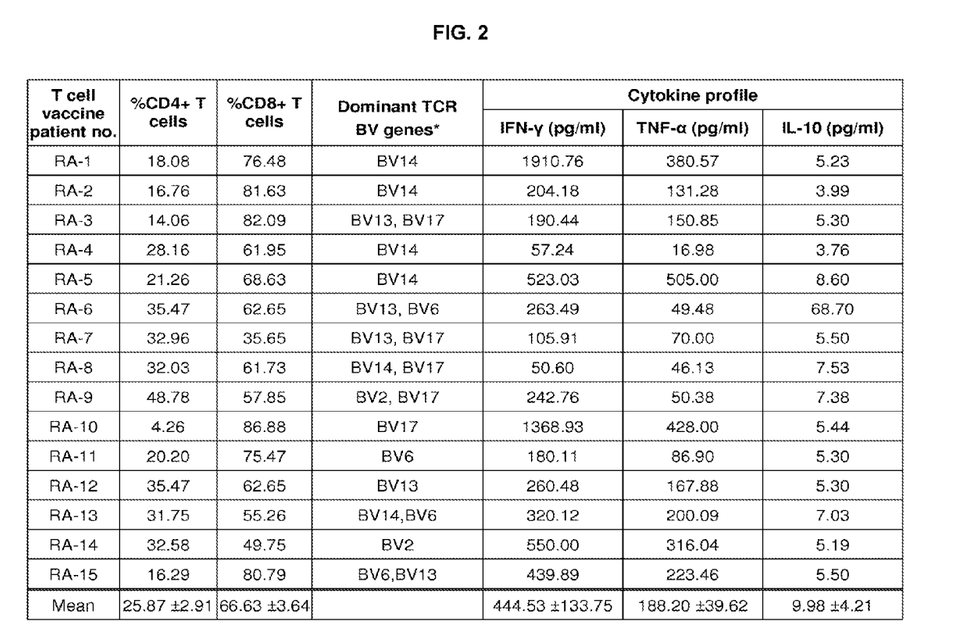
FIG. 2 provides Table 2, which shows the characteristics of the T cell vaccine, with respect to the percentage of CD4+ and CD8+ T cells, and TCR BV and cytokine gene expression levels.

Table 3 summarizes the characteristics of T cell vaccines derived from 15 RA patients, with respect to the percentage of CD4+ and CD8+ T cells, and TCR BV and cytokine gene expression levels. Individual patient data and means are shown.

In addition, expression levels of the transcription factor Foxp3 were measured by real time PCR. Primer Express software (ABI) was used to design primers from published cDNA sequences. BLASTN searches were conducted on the primer nucleotide sequences to ensure gene specificity. The nucleotide primer sequences for the Foxp3 gene were as follows: sense primer 5'-CGGACCATCTTCTGGATGAG-3' (SEQ ID NO: 15), antisense primer 5'-TTGTCGGATGATGCCACAG-3' (SEQ ID NO: 16). The nucleotide probe sequence was as follows: FAM5'-CTGGAGAAG-GAGAAGCTGAGTGCCA-3' (SEQ ID NO: 17) TRMRA. Initial PCR amplification of cDNA with the primers yielded gene products of the expected size on 2% agarose gel. This validated the use of these primers for real time PCR analysis of Foxp3.

Relative quantification of gene expression was performed using the Applied Biosystems ABI Prism 7900 sequence detection system. SYBR Green master mix (ABI) was used for real-time RT-PCR to detect the abundance of PCR products among samples. Thermocycler conditions comprised an initial holding temperature of 50° C. for 2 minutes, then 95° C. for 10 minutes. These were followed by a 2-step PCR program consisting of 95° C. for 15 seconds, and 60° C. for 60 seconds for 40 cycles. Data were collected and quantitatively analyzed on an ABI Prism 7900 HT Sequence Detection System (ABI). The HPRT gene was used as an endogenous control to normalize for differences in the amount of total RNA in each sample. TaqMan HPRT gene primers and a 5'-VIC-labeled MGB probe were used according to the manufacturer's instructions (ABI). All quantities were expressed as n-fold relative to a calibrator.

No Foxp3 expression was detected in the T cell vaccines made from the RA patients.

Example 2

Procedure for Treating Rheumatoid Arthritis

For each treatment, an aliquot of T cell stock was thawed and activated for the preparation of fresh T cell vaccine. To this end, approximately 10 million T cells (one aliquot) were cultured in the presence of 2 μg/ml PHA and 100 IU/ml recombinant IL-2 (Proleukine®, Chiron) for 4-5 days to reach 40-50 million activated T cells. Activated T cells were then washed four times in RPMI medium by centrifugation and were resuspended in medical-grade sterile saline. Cells were packed in syringes and irradiated at 10,000 rads. Irradiation was controlled by RadTag™ (MDS Nordion) to insure sufficient dosage/exposure. After irradiation, each vaccine was subject to final release testing (including Gram stain, sterility testing and T cell identity testing). Five inoculations were given subcutaneously at $30\text{-}45 \times 10^6$ T cells for each vaccination at a monthly interval during the active immunization phase, followed by two booster inoculations with the same dose at month 6 and month 9. For each vaccination, subjects were placed in an out-patient unit for 12 hours to observe any potential acute reactions.

Example 3

Effects of Treatment with the T Cell Vaccine

1. Phenotypic and Cytokine Profile

In one experiment, PBMC samples were obtained from 15 subjects treated with the T cell vaccine. Phenotypic expression was analyzed as described in Example 1. CD45RA/CD45RO antibodies were obtained from BD Biosciences. Samples were obtained prior to treatment (baseline), and at 3-month intervals over a 12-month period.

Post-treatment PBMC samples showed a significant increase in the ratio of CD45RA+/CD45RO+ T cells (4.1±0.6 at month 12 vs. 1.8±0.4 at baseline) while the ratio of CD4 to CD8 T cells remained largely unchanged.

In another experiment, ELISA was used as described above in Example 1 to measure cytokine levels in post-vaccination PBMC samples. This experiment showed that serum IL-12 concentrations decreased significantly from 71.3±26.7 pg/ml at baseline to less than 40 pg/ml at month 3 and subsequent time points following T cell vaccination. Levels of IL-10, interferon-γ, TNF-α and IL-5 were below the lower limits of detection.

Additionally, mRNA expression of the indicated cytokines in PBMC was analyzed in T cell-treated RA patients by real-time PCR at baseline and months 3, 6, 9 and 12 using cytokine gene-specific primers and SYBR Green master mix (Applied Biosystems). The GAPDH gene was used as an endogenous control to normalize for differences in the amount of total RNA in each sample. The PCR conditions and the method of calculation employed here were similar to those previously described in Example 1.

Figure 1:
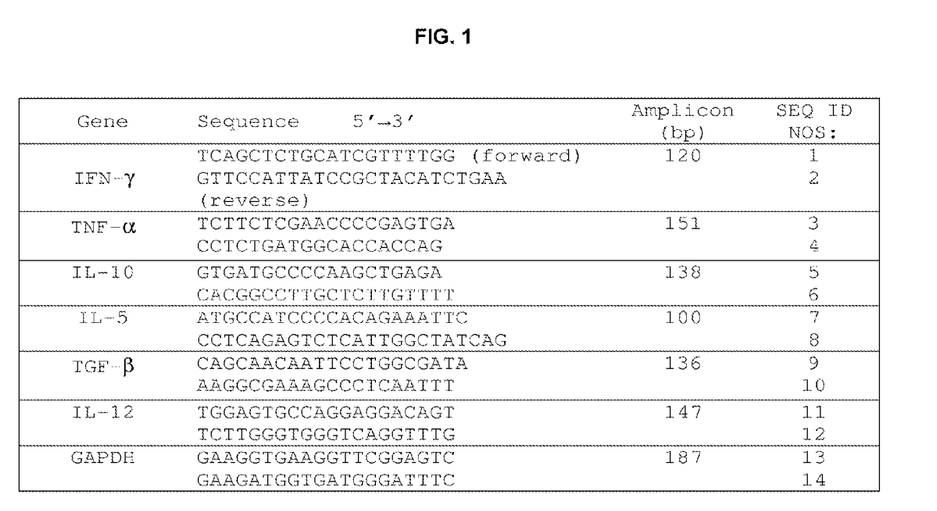
FIG. 1 provides Table 1, which shows the nucleotide sequences of the primers used to measure cytokine gene expression levels.

This highly sensitive real-time PCR revealed a significantly altered cytokine profile, as evident by increased mRNA expression of IL-10, IL-5 and TGF-β and decreased IL-12, TNF-α and interferon-γ at months 3, 6, 9 and 12 post-vaccination PBMC (FIG. 1).

2. Regulatory Immune Response to Treatment with the T Cell Vaccine

In another experiment, CD4+ and CD8+ T cells were prepared from freshly isolated PBMC of T cell-vaccinated RA patients by depleting cells expressing CD8 or CD4, CD14, CD16, CD19, CD36, CD56, CD123, TCRγ/δ, and Glycophorin A using No-touch T cell isolation kits (Miltenyi Biotec). The purity of the resulting CD4+ and CD8+ T cells was 95%-98% as determined by flow cytometry using specific antibodies.

To measure levels of CD4+ regulatory T cells secreting IL-10, ELISPOT assays were used. Purified CD4+ T cells were plated out at the appropriate cell densities in triplicate, and co-cultured with irradiated autologous vaccine or non-specific T cell targets in nitrocellulose-coated microtiter plates pre-treated with anti human IL-10 mAb (BD Pharmingen). To measure CD8+ Granzyme B-secreting T cells, purified CD8+ T cells were co-cultured at a pre-determined density of 100,000 cells/well with irradiated autologous vaccine T cells (100,000 cells/well) in plates pre-coated with anti Granzyme B mAb (BD Parmingen). In all experiments, RPMI medium containing 5% human AB serum was used. Plates were incubated at 37° C. for 4 hours for Granzyme B or 48 hours for IL-10. Biotin-labeled secondary mAbs were added, followed by streptavidin-alkalinephosphatase and substrate to develop an optimal color reaction. Positively stained spots were quantified using Immunospot (CTL Technology) equipped with a high-resolution lens camera and analytical software. Mean number of spots/well was calculated, and net counts were established after subtracting background signal. The frequency was expressed as specific spot-forming cells per million PBMC (ie, purified CD4+ or CD8+ T cells).

FIG. 2 shows that the frequency of both CD8+ cytotoxic anti-idiotypic T cells and CD4+ IL-10-secreting T cells was significantly increased at every time point after T cell vaccination (months 3, 6, 9 and 12) compared to baseline (month 0) in paired specimens (p<0.05).

Additionally, the CD4+CD25+ regulatory T cell response at baseline and at months 3, 6, 9 and 12 was assessed. After isolating CD4+ T cells as described above, CD4+CD25+ T cells were subsequently isolated by positive selection using CD25 microbeads (Miltenyi Biotec). Foxp3 mRNA expression levels were detected in isolated CD4+ and CD4+CD25+ T cells via real time PCR as described above in Example 1.

In yet another experiment, purified CD4+CD25+ T cells were used as responders in functional analysis. CD4+CD25+ T cell preparations were subjected to intracellular staining of Foxp3 using an anti-human Foxp3 staining set (eBioscience), according to manufacturer's instruction. CD25− T cells (10, 000 cells/well) were cultured in the presence of CD4+CD25+ T cells (10,000 cells/well), anti-CD3 and anti-CD28 antibodies (1 μg/ml, eBioscience), and irradiated autologous APCs (50,000 cells/well) for 72 hours in RPMI 1640 medium containing 5% human AB serum and 100 IU/ml IL-2. The ability of CD4+CD25+ T cells to suppress the proliferation of CD25− T cells was determined by [3H] thymidine incorporation. During the final 16-18 hours of the functional assays, 1 μCi [3H] thymidine was added and cell proliferation was measured by scintillation counting. The results were calculated as % inhibition as follows: [1−(experimental CPM/control CPM)]×100%.

Although the phenotypic analysis indicated a slight increase of CD4+CD25+ T cells in the peripheral blood specimens obtained from patients after T cell vaccination (an average of 5.75% at month 12 vs. 3.76% at baseline), it was indistinguishable between CD4+CD25+ regulatory T cells and in vivo-activated non-regulatory T cells.

Figure 3:
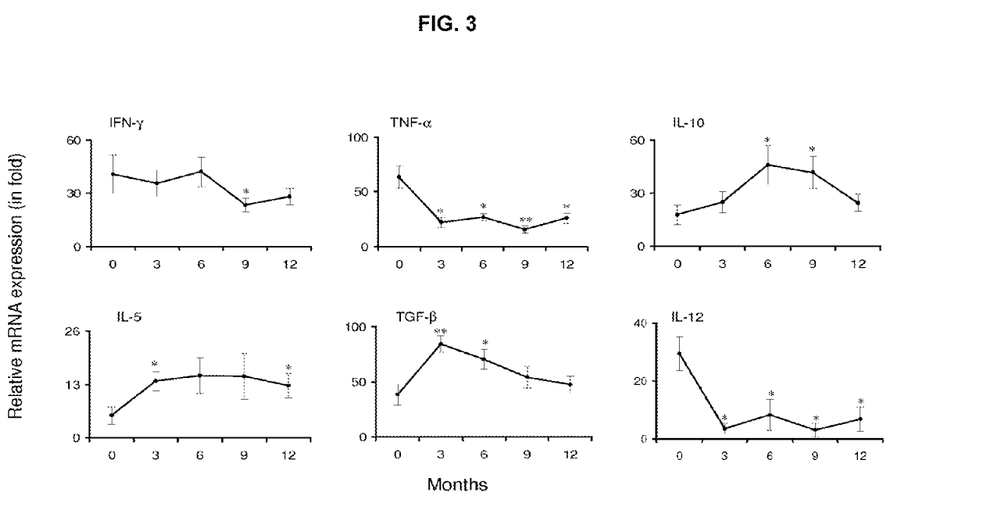
FIG. 3 shows the altered cytokine profile of peripheral blood mononuclear cells (PBMC) following treatment of subjects with the T cell composition. RNA was extracted from PBMC specimens of 15 subjects with rheumatoid arthritis at baseline and at the indicated time points after treatment. mRNA expression levels of the indicated cytokines were determined quantitatively by real-time PCR using specific primers. Asterisks represent significant differences in cytokine expression between baseline and at the indicated time point after treatment with the T cell composition ($*p<0.05$, $**p<0.01$).

Real-time PCR analyses were carried out to determine the expression level of transcription factor Foxp3 in CD4+CD25+ T cells as an indicator of the regulatory properties of these cells. FIG. 3 shows the results of these analyses. The results demonstrated that levels of Foxp3 expression in both unfractionated CD4+ T cells and purified CD4+CD25+ T cells were significantly elevated in post-vaccination samples compared to baseline, as shown by real-time PCR and flow cytometry ($p<0.01$, FIGS. 3A through 3C). Functional analyses with purified CD4+CD25+ T cells from post-vaccination specimens showed significantly increased inhibitory activity on the proliferation of vaccine T cells compared to those obtained from pre-vaccination specimens of the same patients ($p<0.01$, FIG. 3D), indicating that T cell vaccination induced CD4+CD25+ regulatory T cell response.

Figure 4:
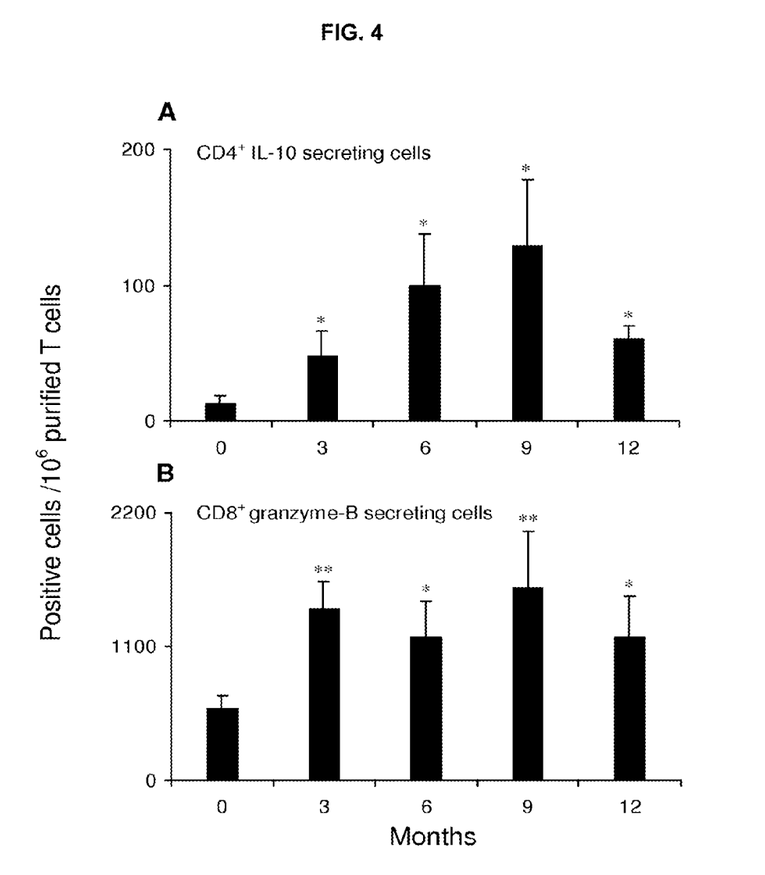
FIG. 4 shows regulatory T cell responses to the T cell vaccine, as measured by the frequency of CD4+ IL-10 secreting cells and the frequency of CD8+ Granzyme B secreting cells. Asterisks represent significant differences in the T cell frequency between baseline and at the indicated time point after T cell vaccination ($*p<0.05$, $**p<0.01$).

3. Effect of the T Cell Vaccine on T Cell Receptor BV Gene Repertoire and Vβ2+ T Cell Induction In another set up experiments, TCR BV gene expression was measured in T cell-treated RA patients at baseline (month 0) and months 3, 6, 9 and 12, using the real-time PCR technique as described in Example 1. Serial real-time PCR analyses revealed that T cell vaccination induced a characteristic shift in BV gene distribution pattern of peripheral T cells (FIG. 4A). In each subject here was a significant reduction in BV14 post-vaccination (mean 16.2% at baseline vs. 3.6% at month 12, $p<0.05$) while TCR BV2 expression increased reciprocally from 16.6% at baseline to 34.2% at month 12 ($p<0.01$).

Additionally, in another set of experiments, after isolating CD4+ T cells using the technique previously described in this example, CD4+ Vb2+ and CD4+ Vb2− T cells were separated by an additional step with Dynabeads coupled with Vb2 monoclonal antibody and subsequently with Detachbeads (Dynal Biotech). The purity of the resulting CD4+ Vb2+ T cells was 95%-98% as determined by flow cytometry using specific antibodies. Foxp3 gene expression in these cells was measured as described in Example 1, and IL-10 secretion by these cells and the cells' inhibitory activity were measured as previously described in this Example.

As shown in FIGS. 4C and 4D, the purified Vb2+ T cell populations derived from post-treatment PBMC were highly enriched for IL-10-secreting T cells and expressed a significantly elevated level of Foxp3 compared to Vb2− T cell fractions of the same PBMC specimens ($p<0.01$). These Vb2+ T cells exhibited the increased inhibitory activity on the proliferation of autologous vaccine T cells or autologous non-specific T cells, which was not seen in the paired CD4+ Vb2− T cell fractions (FIG. 4E).

4. T Cell Reactivity to T Cells of the Vaccine and to IL-2 Receptor Peptides

Figure 5:
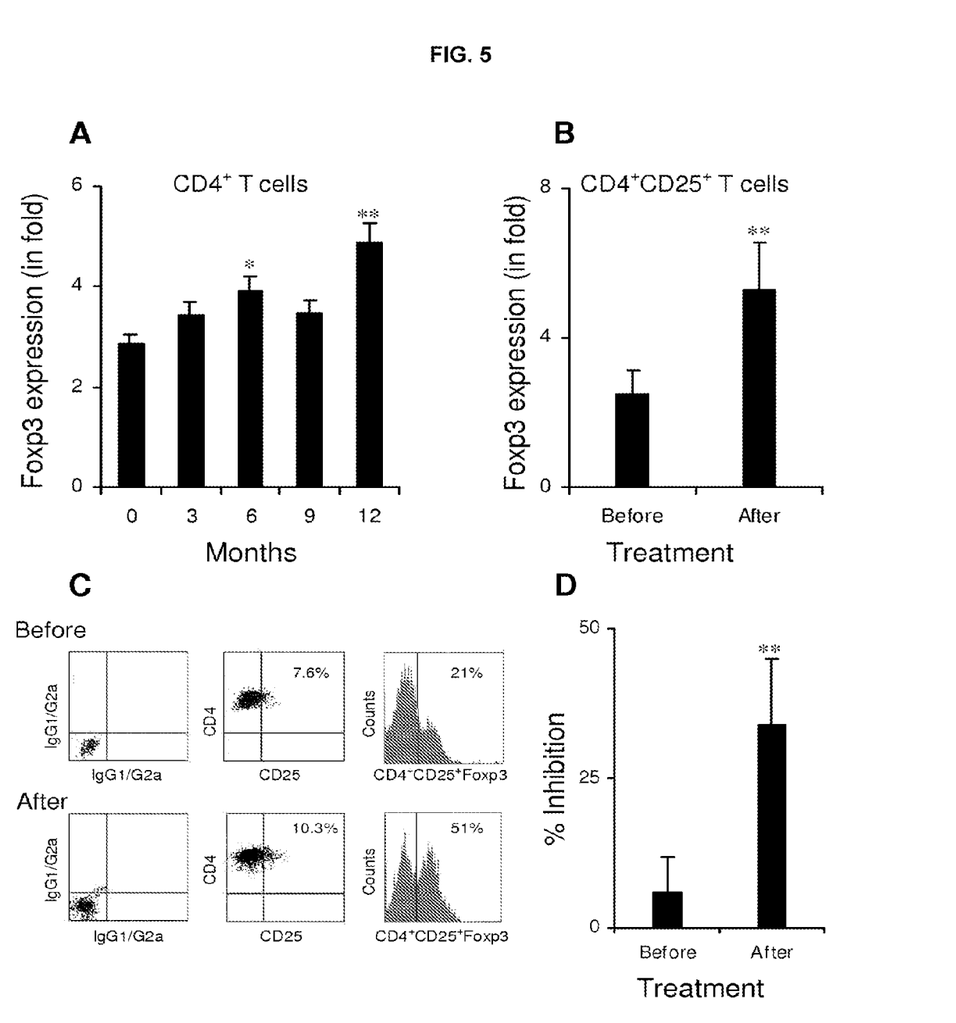
FIG. 5 shows expression of Foxp3 and the inhibitory activity of CD4+CD25+ T cells isolated from peripheral blood. Purified CD4+ T cells (A) and purified CD4+CD25+ T cell fractions (B) were obtained at baseline (Before) and 12 months after T cell vaccination (After) and analyzed for Foxp3 expression levels by real-time PCR. Data were normalized to the HPRT levels and are shown as means±standard error. The same CD4+CD25+ T cell preparations were subjected to intracellular staining of Foxp3 expression (C) and examined for the inhibitory activity on autologous T cell proliferation induced by CD3/CD28 antibodies (D). Asterisks represent significant differences in Foxp3 expression between baseline and at the indicated time point after T cell vaccination ($*p<0.05$, $**p<0.01$).
Figure 6:
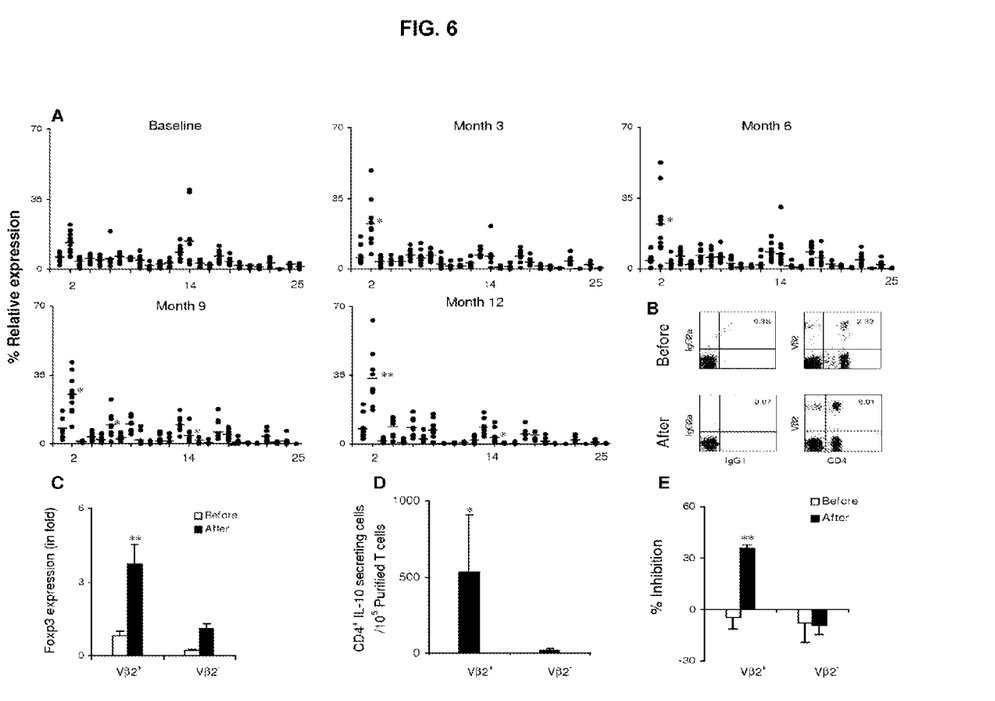
Figure 7:
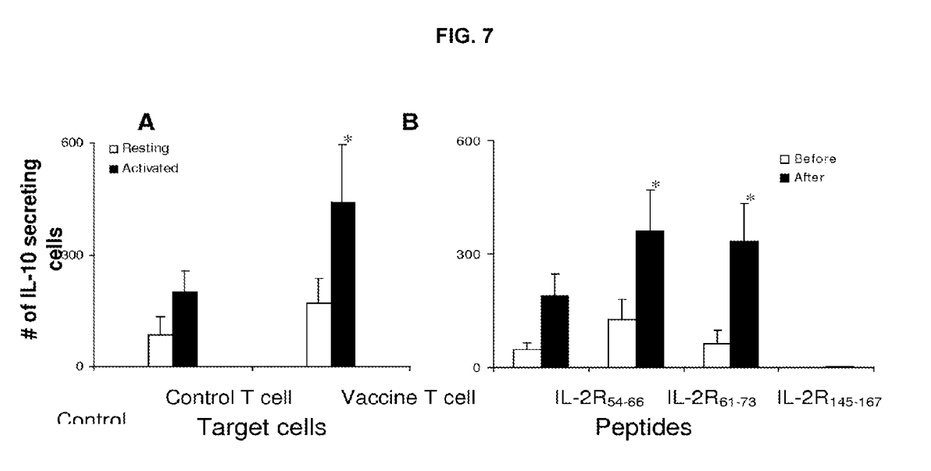
FIG. 7 shows reactivity of IL-10 secreting T cells to T cell targets and to peptides derived from IL-2 receptor. A. PBMC preparations (n=15) obtained before and 12 months after T cell vaccination were analyzed for reactivity to autologous vaccine T cells or unselected T cells that were highly activated by anti-CD3 stimulation (activated state, >90% CD25+ T cells) or allowed to rest (resting state, <20% CD25+ T cells). (B). The same PBMC preparations were examined for reactivity to three peptides derived from IL-2 receptor a-chain, using an irrelevant peptide as a control. The data are expressed as number of IL-10 secreting cells in one million cells tested using ELISPOT. Asterisks represent statistical differences (p<0.05) between the indicated groups.

In yet another set of experiments, CD4+ IL-10 secreting T cells were further characterized to determine their reactivity to resting or activated vaccine T cells and non-selected T cells as autologous target cells. Activated T cell targets (vaccine and non-selected T cells) were prepared by anti-CD3 stimulation and highly expressed CD25 (at least 90%) while less than 20% of resting vaccine T cells and unstimulated T cells derived from PBMC expressed CD25. As illustrated in FIG. 5A, CD4+ T cell preparations obtained from patients after T cell vaccination exhibited significantly increased reactivity to activated, as opposed to, resting vaccine T cells. However, the reactivity pattern was seen with non-selected T cells, suggesting that they recognized marker(s) associated with T cell activation.

It was further determined whether T cell reactivity induced by T cell vaccination recognized epitopes contained in the IL-2 receptor a-chain. For this purpose, three peptides of IL-2 receptor α-chain that had high binding affinity to HLA DRB1*0401 and DRB1*0405 were selected. T cell reactivity to peptides derived from IL-2 receptor a-chain was measured by culturing PBMC in the presence of IL-2 receptor peptides and the control peptides. As shown in FIG. 5B, T cells contained in post-treatment PBMC reacted preferentially to peptides corresponding to residues 61-73 and residues 145-167 of IL-2 receptor a-chain when compared to a control peptide.

5. Clinical Response to Treatment with the T Cell Vaccine

Sixteen patients with RA were included in this study. The diagnosis was made according to the criteria of American College of Rheumatology (ACR; Hochberg et al, *Arthritis Rheum* 1991; 35:498-502). Patients had not received steroids or immunosuppressive treatments 2 months prior to and during the study. Non-steroidal anti-inflammatory drugs and other symptomatic treatments were given to alleviate symptoms. As required by the protocol, patients who did not reach minimum clinical improvement as measured by ACR20 within 6 to 8 weeks were withdrawn from the study and given standard immunosuppressive treatments. The study protocol was approved by the Medical Ethics Review Board of Shanghai Institutes of Biological Sciences, Chinese Academy of Sciences. Consent was obtained from all participating patients after explaining the study protocol. One patient dropped out from the study as a result of failing to reach ACR20 within eight weeks, while the remaining 15 patients (one male and 14 females) continued with the study protocol. Mean age of the patients was 51.5 years (range 30-67) with average disease duration of 10.7 years (range 1-29). Eleven of fifteen patients were RF positive with a medium titer of 472 IU/ml (range 110-2201). Mean serum level of C-reactive protein and erythrocyte sentiment rate were 54.5 μg/ml and 57.4 mm/h, respectively. In these patients, the DRB1*0405 and DRB1*09012 genotypes were preferentially expressed.

Clinical outcome measures included ACR20, ACR50 and ACR70 responder rates at months 3, 6, 9 and 12, for an intent-to-treat population of patients. To be classified as having achieved ACR20, patients were required to complete one-year treatment and meet ACR20 that was defined by 20% improvement in tender and swollen joint counts and 20% improvement in three of the following five criteria: patient global assessment, physician global assessment, pain intensity, physical function or disability measure and level of acute-phase reactant (Hochberg et al, *Arthritis Rheum* 1992; 35:498-502). The ACR50 and ACR70 responder rates were defined as at least 50% and 70% improvement, respectively, using the same criteria as described above. The measurements included a change from baseline to each of months 3, 6, 9 and 12, in each individual component of the ACR response criteria, and the change from baseline to one year (and to months 3, 6, and 9) in levels of erythrocyte sentiment rate, C-reactive protein and rheumatoid factor. All ACR assessments were performed by the same clinical investigators throughout the study.

Throughout the study, no adverse reactions were observed clinically and in monthly routine laboratory assays that included standard hematological, blood chemistry, liver and renal functions. Table 4 shows the clinical assessment of the T cell-vaccinated patients. An ACR20 response was attained relatively early in a large proportion of patients (11/15, 73.3%) at month 3 and maintained throughout the study. In contrast, a substantial response (ACR50 and ACR70) was only achieved after the forth immunization at month 6 and reached 66.7% and 53.3%, respectively, at the end of one-year study. Overall there was a significant reduction ($p<0.01$) in swollen and tender joint counts and in other clinical variables post T cell vaccination. The observed clinical improvements were associated with a significant reduction from baseline in serum markers of inflammation ($p<0.05$), including erythrocyte sentiment rate, C-reactive protein and rheumatoid factor.

The invention claimed is:

1. A method of treating a patient with rheumatoid arthritis comprising
   (i) activating synovial T cells in the presence of peripheral blood mononuclear cells and IL-2, wherein the synovial T cells and peripheral blood mononuclear cells are obtained from a patient with rheumatoid arthritis, and wherein the peripheral blood mononuclear cells are attenuated with irradiation or chemical treatment to be replication incompetent yet viable;
   (ii) expanding the activated T cells of (i) in the presence of a T cell mitogen and IL2, wherein the expanded cells are characterized by the following:
      (a) the T cells secrete TNF-α and γ-interferon;
      (b) the T cells comprise at least 4% CD4+ T cells;
      (c) the T cells comprise at least 4% CD8+ T cells; or
      (d) a combination thereof;
   (iii) attenuating the expanded T cells of (ii) with irradiation or chemical treatment to make the T cells replication incompetent yet viable; and
   (iv) co-administering the attenuated T cells of (iii) with an IL2 receptor a-chain peptide corresponding to residues 61-73 or residues 145-167 of the IL2 receptor α-chain to the patient with rheumatoid arthritis, thereby treating rheumatoid arthritis in the patient.

2. The method of claim 1, wherein the IL2 receptor α-chain peptide corresponds to residues 145-167 of the IL2 receptor α-chain.

* * * * *

UNITED STATES PATENT AND TRADEMARK OFFICE
CERTIFICATE OF CORRECTION

PATENT NO.       : 8,629,108 B2  
APPLICATION NO. : 12/306894  
DATED            : January 14, 2014  
INVENTOR(S)      : Zang et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1230 days.

Signed and Sealed this
Twenty-second Day of September, 2015

Michelle K. Lee
*Director of the United States Patent and Trademark Office*

```
                            SEQUENCE LISTING

<160> NUMBER OF SEQ ID NOS: 17

<210> SEQ ID NO 1
<211> LENGTH: 20
<212> TYPE: DNA
<213> ORGANISM: Artificial
<220> FEATURE:
<223> OTHER INFORMATION: Synthetic

<400> SEQUENCE: 1
tcagctctgc atcgttttgg                                                   20

<210> SEQ ID NO 2
<211> LENGTH: 24
<212> TYPE: DNA
<213> ORGANISM: Artificial
<220> FEATURE:
<223> OTHER INFORMATION: Synthetic

<400> SEQUENCE: 2
gttccattat ccgctacatc tgaa                                              24

<210> SEQ ID NO 3
<211> LENGTH: 20
<212> TYPE: DNA
<213> ORGANISM: Artificial
<220> FEATURE:
<223> OTHER INFORMATION: Synthetic

<400> SEQUENCE: 3
tcttctcgaa ccccgagtga                                                   20

<210> SEQ ID NO 4
<211> LENGTH: 19
<212> TYPE: DNA
<213> ORGANISM: Artificial
<220> FEATURE:
<223> OTHER INFORMATION: Synthetic

<400> SEQUENCE: 4
cctctgatgg caccaccag                                                    19

<210> SEQ ID NO 5
<211> LENGTH: 19
<212> TYPE: DNA
<213> ORGANISM: Artificial
<220> FEATURE:
<223> OTHER INFORMATION: Synthetic

<400> SEQUENCE: 5
gtgatgcccc aagctgaga                                                    19

<210> SEQ ID NO 6
<211> LENGTH: 20
```

```
<212> TYPE: DNA
<213> ORGANISM: Artificial
<220> FEATURE:
<223> OTHER INFORMATION: Synthetic

<400> SEQUENCE: 6
cacggccttg ctcttgtttt                                                20

<210> SEQ ID NO 7
<211> LENGTH: 21
<212> TYPE: DNA
<213> ORGANISM: Artificial
<220> FEATURE:
<223> OTHER INFORMATION: Synthetic

<400> SEQUENCE: 7
atgccatccc cacagaaatt c                                              21

<210> SEQ ID NO 8
<211> LENGTH: 24
<212> TYPE: DNA
<213> ORGANISM: Artificial
<220> FEATURE:
<223> OTHER INFORMATION: Synthetic

<400> SEQUENCE: 8
cctcagagtc tcattggcta tcag                                           24

<210> SEQ ID NO 9
<211> LENGTH: 21
<212> TYPE: DNA
<213> ORGANISM: Artificial
<220> FEATURE:
<223> OTHER INFORMATION: Synthetic

<400> SEQUENCE: 9
cagcaacaat tcctggcgat a                                              21

<210> SEQ ID NO 10
<211> LENGTH: 20
<212> TYPE: DNA
<213> ORGANISM: Artificial
<220> FEATURE:
<223> OTHER INFORMATION: Synthetic

<400> SEQUENCE: 10
aaggcgaaag ccctcaattt                                                20

<210> SEQ ID NO 11
<211> LENGTH: 20
<212> TYPE: DNA
<213> ORGANISM: Artificial
<220> FEATURE:
<223> OTHER INFORMATION: Synthetic

<400> SEQUENCE: 11
tggagtgcca ggaggacagt                                                20

<210> SEQ ID NO 12
<211> LENGTH: 20
<212> TYPE: DNA
<213> ORGANISM: Artificial
<220> FEATURE:
<223> OTHER INFORMATION: Synthetic

<400> SEQUENCE: 12
tcttgggtgg gtcaggtttg                                                20
```

```
<210> SEQ ID NO 13
<211> LENGTH: 20
<212> TYPE: DNA
<213> ORGANISM: Artificial
<220> FEATURE:
<223> OTHER INFORMATION: Synthetic

<400> SEQUENCE: 13
gaaggtgaag gttcggagtc                                                    20

<210> SEQ ID NO 14
<211> LENGTH: 20
<212> TYPE: DNA
<213> ORGANISM: Artificial
<220> FEATURE:
<223> OTHER INFORMATION: Synthetic

<400> SEQUENCE: 14
gaagatggtg atgggatttc                                                    20

<210> SEQ ID NO 15
<211> LENGTH: 20
<212> TYPE: DNA
<213> ORGANISM: Artificial
<220> FEATURE:
<223> OTHER INFORMATION: Synthetic

<400> SEQUENCE: 15
cggaccatct tctggatgag                                                    20

<210> SEQ ID NO 16
<211> LENGTH: 19
<212> TYPE: DNA
<213> ORGANISM: Artificial
<220> FEATURE:
<223> OTHER INFORMATION: Synthetic

<400> SEQUENCE: 16
ttgtcggatg atgccacag                                                     19

<210> SEQ ID NO 17
<211> LENGTH: 25
<212> TYPE: DNA
<213> ORGANISM: Artificial
<220> FEATURE:
<223> OTHER INFORMATION: Synthetic

<400> SEQUENCE: 17
ctggagaagg agaagctgag tgcca                                              25
```